United States Patent [19]

Fox, Jr. et al.

[11] Patent Number: 4,952,411
[45] Date of Patent: Aug. 28, 1990

[54] METHOD OF INHIBITING THE TRANSMISSION OF AIDS VIRUS

[75] Inventors: Charles L. Fox, Jr., New York, N.Y.; Shanta M. Modak, River Edge, N.J.

[73] Assignee: Trustees of Columbia University in the City of New York, Morningside Heights, N.Y.

[21] Appl. No.: 262,165

[22] Filed: Oct. 18, 1988

Related U.S. Application Data

[63] Continuation-in-part of Ser. No. 18,624, Feb. 25, 1987, abandoned.

[51] Int. Cl.$^5$ .................... A61K 33/38; A61K 31/56; A61K 31/28; A61K 31/155
[52] U.S. Cl. .................................... 424/618; 514/169; 514/495; 514/635
[58] Field of Search ............... 514/157, 495, 169, 635; 424/618

[56] References Cited

U.S. PATENT DOCUMENTS 3,761,590 9/1973 Fox, Jr. ................................ 514/157
4,415,565 11/1983 Wysur ................................ 514/157

OTHER PUBLICATIONS

Chem. Abstracts, 83:716206, (1975).
Wysur, Antibiotics, vol. VI, Springer-Verlag, Berlin, pp. 200–232, (1983).
Chem. Abstracts, 102(15):128281j, (1985), Boudouma et al.
Chem. Abstracts, 101(19):221999p, (1984), Queno et al.

*Primary Examiner*—Jerome D. Goldberg
*Assistant Examiner*—Raymond J. Henley, III
*Attorney, Agent, or Firm*—Brumbaugh Graves et al.

[57] ABSTRACT

An inexpensive, easily available and convenient method of inhibiting the transmission of the AIDS virus in humans as a result of sexual intercourse is provided. The method relies upon a dual mode of action of antiviral compositions comprising silver salts, such as silver sulfadiazine, alone or in combination with chlorhexidine or sodium deoxycholate. These composition are effective to reduce the infectivity of the AIDS virus and also kill the causative organisms of many other sexually transmitted diseases (STD). The method of the invention is therefore useful to reduce the immediate risk of AIDS transmission. It also reduces future risk of AIDS transmission by eliminating STD causing organisms which increase the risk of AIDS.

14 Claims, 1 Drawing Sheet

METHOD OF INHIBITING THE TRANSMISSION OF AIDS VIRUS

BACKGROUND OF THE INVENTION

This application is a continuation-in-part of prior U.S. patent application Ser. No. 018,624, filed Feb. 25, 1987 and abandoned upon the filing of this application.

BACKGROUND OF THE INVENTION

The present invention relates to a method of inhibiting the transmission of Acquired Immunodeficiency Syndrome (AIDS).

AIDS is a fatal catastrophic disease that presently infects millions of people worldwide. Although initially concentrated in central Africa and in certain high risk groups in other geographic areas including the United States, AIDS is now spreading to other areas and is appearing in individuals who are not members of the recognized risk groups. As a result, major efforts are being made to develop methods of preventing the transmission of AIDS, methods of curing AIDS once contracted, and methods of ameliorating the symptoms of AIDS. To date, however, AIDS has proven difficult to treat or prevent.

AIDS is caused by a virus. This virus has been referred to by a number of names in the literature, including HIV (human immunodeficiency virus) LAV (lymphadenopathy-associated virus), ARV (AIDS-related virus) and HTLV-III (human T-cell leukemia virus-III). For simplicity, the virus causing AIDS will be referred to herein as the AIDS virus.

It is generally known that viruses can be divided into two groups based upon the nature of the virus' genetic material. Some viruses are DNA viruses, that is there genetic material is deoxyribonucleic acid, while others are RNA (ribonucleic acid) viruses. The RNA viruses can further be divided into two groups, those in which replication of the viral genome proceeds by making an RNA copy directly from the RNA genome and those in which a DNA intermediate is involved. This latter type of RNA virus is called a retrovirus.

The AIDS virus is a retrovirus Thus, like other retroviruses, it has an enzyme called reverse transcriptase (or RNA-dependent DNA polymerase) which catalyzes transcription of viral RNA into double helical DNA. This DNA sequence is integrated into the genome of the infected cell where it is known as a provirus. Subsequent transcription of this provirus by the transcription mechanism of the infected cell produces new viral RNA for packaging into new virus particles.

Because the AIDS virus may lie dormant in an infected cell in the form of a provirus for extended periods of time, it has been difficult to establish the precise routes by which AIDS is spread. It is known, however, that AIDS can be transmitted to a person by transfusing that person with blood containing the AIDS virus. AIDS can also be transmitted to a person through homosexual or heterosexual intercourse with a partner infected with the AIDS virus. Transmission of the AIDS virus is facilitated by preexisting sexually transmitted diseases (STD's) other than AIDS, for example gonorrhea. Further, scientists suspect that the AIDS virus is spread easily during sexual intercourse due to tearing of tissue which would abet entry of the AIDS virus into the blood stream.

In response to the growing threat of AIDS transmission, the use of condoms during sexual intercourse has been suggested as a means of preventing transmission of the AIDS virus. Improper use of condoms, or their perforation during intercourse renders them only partially effective. Accordingly, there is a pressing need for a better method of inhibiting the transmission of the AIDS virus in humans during sexual intercourse and during surgical procedures on infected patients. It is an object of the present invention to provide such a method.

SUMMARY OF THE INVENTION

The present invention provides an inexpensive, easily available and convenient method of inhibiting the transmission of the AIDS virus in humans as a result of sexual intercourse. The method relies upon a dual mode of action of particular compounds and combinations thereof which results in a rapid killing action within minutes. These compounds are effective to reduce the infectivity of the AIDS virus and also kill the causative organisms of many other STD's after short exposure. The method of the invention is therefore useful to reduce the immediate risk of AIDS transmission. It also reduces future risk of AIDS transmission by eliminating STD causing organisms which increase the risk of AIDS.

Central to the method of the invention is the discovery that silver salts, such as silver sulfadiazine (AgSD), are effective antiviral agents against retroviruses including the AIDS virus. Such materials had previously been recognized as antibacterial agents useful in treating burns in man and animal. C.L. Fox, Jr., U.S. Pat. No. 3,761,590. AgSD has also been shown to be effective against certain viruses such as herpes simplex and herpes zoster and against the causative organisms of many STD's including *Candida albicans, Treponema pallidum* and gonorrhea. U.S. Pat. No. 4,415,565 of Wysor shows further antiviral activity of AgSD against certain RNA viruses, but none of these are retroviruses. Thus, while AgSD is a well studied material, there was no basis to expect that it would have activity against the AIDS retrovirus which has proven so difficult to inhibit or destroy.

We have also found that combinations of silver compounds such as AgSD with other antibacterial agents lead to an unexpected enhancement of the antiviral activity of AgSD and also in a rapid killing action. Specifically, AgSD in combination with chlorhexidine, a broad spectrum antibacterial, is substantially more effective for reducing the infectivity of the AIDS virus than AgSD alone, despite the fact the chlorhexidine alone has no effect on infectivity of AIDS virus under the same conditions. Increased effectiveness was also noted for combinations of AgSD with detergents such as deoxycholate.

In view of these findings, the invention contemplates a method of inhibiting the transmission of AIDS in humans upon sexual intercourse comprising topically applying an effective antiviral amount of a silver salt such as silver sulfadiazine, alone or in combination with other agents such as chlorhexidine or deoxycholate, to a sexual canal of a human prior to or during sexual intercourse. This application can be carried out by introducing a cream or foam into the sexual canal, or by coating the inhibitory composition onto a condom or other device that is inserted into the sexual canal.

DETAILED DESCRIPTION OF THE INVENTION

Figure 1:
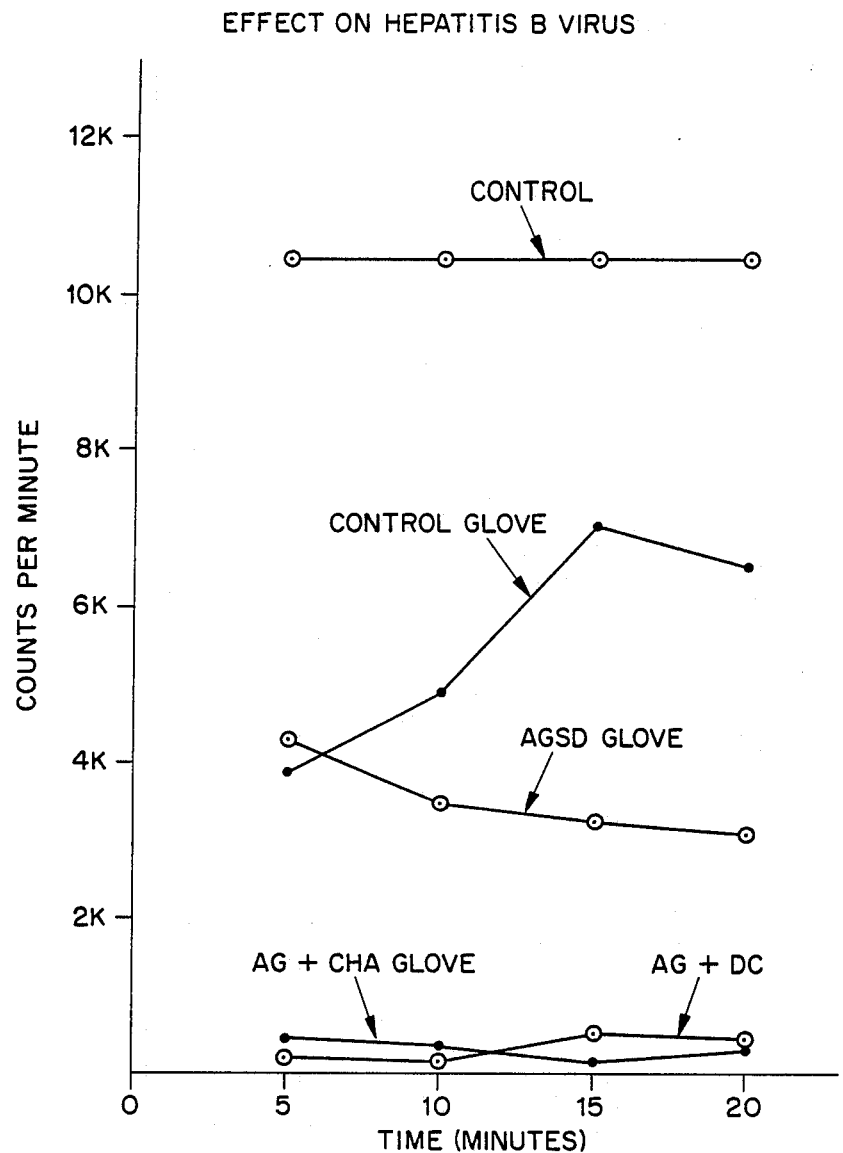
FIG. 1 is a graph of the rate of incorporation of radiolabeled thymidine by hepatitis B virus following exposure of the virus to AgSD alone or in combination with other agents.

As noted above, the method of the present invention of inhibiting the transmission of AIDS virus in humans upon sexual intercourse comprises topically applying an effective antiviral amount of an antiviral composition comprising a silver salt, alone or in combination with other active ingredients, to a sexual canal of a human prior to or during sexual intercourse. As used in this application, the term sexual canal refers to either a vaginal or an anal canal.

The antiviral composition used in the method of the invention comprises a silver salt. While the examples hereinbelow use one specific silver salt, AgSD, other silver salts may also be used. Other suitable silver salts include silver acetate, silver benzoate, silver carbonate, silver chloride, silver iodate, silver iodide, silver lactate, silver laurate, silver nitrate, silver oxide, silver palmitate, and silver salts of proteins.

The antiviral composition used in the method of the invention preferably also comprises one or more additional ingredients which enhance the antiviral effectiveness of the silver salt. Thus, the antiviral composition may contain a biguanidine such as chlorhexidine, or detergents such as deoxycholate or benzalkonium chloride. Suitable salts of each of these materials may also be used.

The antiviral composition may also include other materials which are effective against STD-causing organisms which will reduce the long term risk of AIDS infection. Examples of such materials include nonoxynol, which is effective against gonococcus and quinolones which are effective against numerous STD-causing organisms. It should be noted that chlorhexidine and the detergents noted above are also effective against a variety of STD-causing organisms, including herpes simplex virus (HSV) and *Candida albicans.*

The antiviral compositions for use in the invention can be applied as (a) a dispersion in a water-dispersible hydrophilic carrier; (b) as a dispersion in a substantially water insoluble carrier; (c) as a dispersion in a semi-soft or cream-like water-dispersible or water-soluble oil-in-water emulsion carrier; of (d) as a dispersion in an aqueous sucrose carrier, e.g. an approximately 25%–50% by weight aqueous sucrose solution Specific examples of formulating silver sulfadiazine in various carriers are provided in U.S. Pat. No. 3,761,590 which is incorporated herein by reference. The carrier will preferably contain from about 0.1 to about 10% by weight of the silver salt and up to 2% of other active agents The antiviral composition useful in the method of the invention can be contained in a squeezable tube having an applicator nozzle. This facilitates topical application of the composition to the sexual canal prior to intercourse by inserting the nozzle into the sexual canal and squeezing the tube to force the antiviral composition into the sexual canal. Alternatively, the antiviral can be applied with any of various known applicators for delivering drugs into a sexual canal. The antiviral composition can also be topically applied during sexual intercourse by coating the penis itself or coating a condom with a lubricant material, such as K-Y Jelly (Johnson & Johnson), that contains the silver salt.

The antiviral composition of the invention may also be introduced into the sexual canal as a coating on a device intended for insertion in the sexual canal. Examples of such devices include condoms, medical gloves, and diaphragms. Such devices may be coated or impregnated with the antiviral composition by spraying the completed device or by incorporating the antiviral composition during manufacture. Specific techniques for preparing the devices are described in U.S. patent application Ser. No 154,920, filed Feb. 11, 1988, and its combination-in-part filed Oct. 14, 1988, both of which are incorporated herein by reference.

The experimental results which demonstrate the effectiveness of the claimed method are set forth below. These tests involve the AIDS virus or a recognized model system for the AIDS virus. Further, although the tests with the AIDS virus itself are necessarily in vitro tests in view of the catastrophic consequences of AIDS, these in vitro tests are highly predictive of and correlate with in vivo efficacy. They thus support the surprising finding that compositions containing silver salts can be used to inhibit transmission of AIDS as a result of sexual intercourse.

EXAMPLE 1

The effectiveness of AgSD against the AIDS virus in vitro was assessed by testing the infectivity of samples of HTLV-III in H9 cells after exposure to AgSD for 10 minutes. Due to the relatively low titers achievable with the AIDS virus, it was necessary to devise means for separating the bulk of the AgSD from the virus to be assayed. After a number of preliminary experiments, it was found that the best method of those investigated was to rapidly pass the AgSD/AIDS virus mixture over a Sephadex G-25M column, recover the AIDS virus containing void volume and precipitate the virus using polyethylene glycol (PEG).

To determine recovery of the virus using this method, a control preparation containing virus but no AgSD was similarly processed.

It was also necessary to confirm that this procedure was effective to remove all of the AgSD. This was accomplished using "Stop Controls". This involved processing AgSD alone through the column, precipitating the same fraction with PEG and then adding active AIDS virus to the precipitate. If the titer of the stop control had been similar to the control preparation containing virus but no AgSD it would have indicated that little or no AgSD was present in the precipitate. In fact, however, the titer was substantially lower in the stop controls (Samples 4 and 6) than in the corresponding test samples without silver sulfadiazine (Samples 1 and 2). This indicates that some of the silver sulfadiazine is not being separated. While this means that virus killing occurred over a longer period than the ten minute contact time, it also suggests that the virucidal activity is fairly strong to persist even at the reduced levels.

The specific tests conducted are summarized in Table 1. For each sample to which virus was added initially, the virus sample was a stock solution prepared from a 10,000 fold concentrate of HTLV-III obtained from Bionetics Research. This material was diluted 1:10 with Conditioned Infection Medium (CIM) to form a stock solution with an actual virus titer of $10^{5.5}$/ml. Two AgSD stock preparations were also prepared, a 1% by weight in 50% by weight aqueous sucrose preparation and an 0.5% by weight in 25% by weight aqueous sucrose preparation.

To conduct the tests, 60 µl aliquots of the virus stock were placed in microfuge tubes as samples 1-3 and 6 as indicated in Table 1. This was mixed with 540 µl of the respective AgSD preparations in tubes 3 and 5 and with 540 µl of CIM in tubes 1 and 2. Tubes 4 and 6 each received 600 µl of the respective AgSD preparations, but no virus. Each tube was then mixed with a vortex mixer and allowed to incubate for 10 minutes at room temperature.

To separate the AgSD from the virus, the contents of each tube containing AgSD then centrifuged in a microfuge for 1 minute, and the supernatants were collected. These supernatants and the entire sample of tube 2 were then introduced onto a Sephadex-25M column. The columns used had a fitted disc at the top of the column and a void volume of approximately 1 ml. These columns are normally stored in sodium azide and had been prepared by washing under sterile conditions with 18 successive 4 ml portions of CIM medium on the day prior to the experiment.

Each of the samples was placed on the column until it passed through the fitted disc. The column was then eluted with 4 ml of CIM medium. The first 3 ml of eluent was discarded and the last ml was collected into a sterile microfuge tube containing 0.35 ml of 30% PEG 6000 in phosphate buffer. These tubes were held at 0° C. for at least 30 minutes and then centrifuged for 1 minute in a microfuge. The pellets were collected and resuspended in either 0.5 ml CIM (samples 2, 3 and 5) or in an HTLV-III containing medium made by diluting 0.7 parts of the virus stock with 6.3 parts of CIM.

Each of the six samples thus prepared was assayed in quadruplicate with 10-fold dilutions in CIM for its ability to infect H9 cells. This was done by adding 50 μl of a preparation containing $2.4\times10^6$/ml H9 cells that had been conditioned in CIM for 1 hour at 37° C. to each 100 μl of sample or dilution. This culture was fed 25 μl of CIM on days 4, 7 and 10. On day 4, cytotoxicity was evaluated by visual examination of the cultures.

The results of these observations are shown in Table 1. As can be clearly seen, AgSD substantially reduced the infectivity of AIDS virus tested without any observation of cytotoxicity.

EXAMPLE 2

The effect of AgSD, chlorhexidine and sodium deoxycholate, both individually and in combination, on the infectivity of the ARV-2 strain of AIDS virus was tested in H9 cells using lower concentrations of drug such as can be practically coated onto a glove or condom or other device. These concentrations were below the level that produced substantial observable cytotoxicity, even during incubation with the virus, and yet were effective at killing the virus.

A stock solution of virus containing 3 to 5 $\times10^4$ infectious virus particles/ml was preincubated with the various drugs as indicated in Table 2 for 15 minutes. The virus sample was then diluted 4-fold in order to reduce the concentrations of the drugs below levels toxic to H9 cells (see Example 3 below) and mixed with 250,000 H9 cells in a total volume of 1 ml. After 24 hours, the cells were assayed to determine the percentage of the culture expressing viral antigen. This time interval was selected as it allows for only a single round of viral infection to have occurred such that the number of cells infected was a direct reflection of the number of infectious virions present in the original sample.

As can be seen from Table 2, AgSD alone at these low concentrations was only slightly effective, but better results were obtained when AgSD was used in combination with either sodium deoxycholate and chlorhexidine. Of particular significance is the marked reduction in infectivity observed for the combination of AgSD (5 μl ml) and chlorhexidine (5 μl ml) since chlorhexidine (10 μml) did not itself reduce viral infectivity.

EXAMPLE 3

The toxicity of the various agents used in the antiviral compositions of the invention to human $T^4$-lymphocytes (H9 cells) and macrophages which are the carriers of the AIDS virus may be relevant to the effectiveness of a drug. This is because killing these cells when present in semen or vaginal fluids may lead to release of virus making it more susceptible to the effects of the drug. With this in mind, the effect of short exposure (10 minutes) of AgSD and other drugs on H9 cells was tested by treating a suspension of H9 cells ($1.6\times10^6$/ml in HBSS) with 50 and 100 μl/ml of each drug or drug combination. After incubating for 10 minutes, the cells were washed twice in thirty volumes of HBSS; resuspended in RPMI 10% FCS+NaPyruvate and plated into 24 well plates at $4\times10^5$ cells/ml. Cell viability was determined after 24 hours and is reported as numbers of viable cells per ml and viable percentage (live cells/live cells+dead cells) in Table 3A. As can be seen, each of the agents tested kills some of the cells, although the most significant killing is observed for 100 μl/ml AgSD and the combination of AgSD and sodium deoxycholate.

The effectiveness of killing of macrophages was also tested as shown in Table 3B. In the experiment, peritonial normal mouse macrophages were enriched by attaching to petri dishes and adjusted to a cell concentration of 5 to $10\times10^6$/ml 0.1 ml aliquots of this suspension were plated in microtiter plates and 10μ and 5μ of each of four samples was added. The control plate received PBS only. After 20 minutes of incubation in a $CO_2$ incubator, the cells were tested for viability using tryphan-blue dye. The percent kill is shown in Table 3B.

EXAMPLE 4

In vivo tests were performed using Rauscher Leukemia Virus (RLV), a recognized retrovirus model (see, e.g., Nature 323, 467–469 (1986); Rupecht et al., Proc. Nat'l. Acad. Sci. USA 82, 7733–7737 (1985)) which is used by the FDA in testing drugs for use in treating AIDS. RLV was introduced into Balb/CICR mice in which it infects the spleen. The level of virus infectivity was quantified by determining the weight increase of the mouse spleen after 20 days from infection.

A preliminary experiment was first carried out to determine the effect of the drugs to be tested on the spleen. Nine sets of five mice each (6 week old female mice) received 0.25 ml injections into the tail vein of one of an extract of a glove treated with one of the following solutions:

1. Silver Sulfadiazine (2%)
2. Sodium Deoxycholate (2%)
3 Chlorhexidine (2%)
4. Silver Sulfadiazine (1%)+Sodium Deoxycholate (1%)
5. Silver Sulfadiazine (1%)+Chlorhexidine (1%)

6. Fusidic Acid (2%)
7. Fusidic Acid (1%)+Chlorhexidine (1%)
8. Saline incubated glove
9. Saline-no glove Each treatment was prepared by incubating 1.5 ml Dulbecco's Phosphate Buffered Saline (PBS) for 10 minutes at 37° C. in the finger tip of a latex glove. After incubation, as much as possible of the material was removed from the glove. 0.4 ml of PBS was then introduced into the glove and this was the sample which was introduced into the animals. The animals that did not receive a clean stick during the injection were excluded from the study. Thus two of the groups only had four animals each that were considered.

Eight days after injection each of the animals was sacrificed and the spleen weights determined for each animal. No increase in spleen weight was observed in any of the groups.

An additional eleven groups of 5 mice each were then used to test the effectiveness of these same compounds against infectivity of RLV. Each treatment was prepared by incubating 0.4 ml sterile PBS containing RVB3 (a strain of RLV) for 10 minutes in a glove tip which had previously had one of drugs or straight PBS incubated in it as described above. Three additional controls, a PBS containing glove with no virus, a virus sample not incubated in a glove, and a PBS sample not incubated in a glove were also run. The mice in this case were sacrificed 20 days after injection and spleen weights determined as shown in Table 4. Each of the materials tested showed a substantial reduction in virus infectivity.

EXAMPLE 5

The combination of AgSD with chlorhexidine and deoxycholate was also found to be particularly effective against several STD-causing organisms. As shown in Tables 5A and 5B silver sulfadiazine in combination with chlorhexidine or sodium deoxycholate is particularly effective against Candida albicans. Similarly, these combinations are effective to kill Gonococcus (Table 6) and herpes virus (Tables 7A and 7B).

EXAMPLE 6

The effect of AgSD alone or in combination with chlorhexidine or sodium deoxycholate on DNA synthesis by Hepatitis B Virus was studied by measuring the rate of incorporation of radiolabeled thymidine. As a result, it was found that the AgSD interferes with the RNA-dependent DNA polymerase of Hepatitis B virus, an interference which is enhanced by using it in combination with either chlorhexidine or sodium deoxycholate (FIG. 1).

TABLE 1

| | | | | | ASSAY MIXTURES AND RESULTS | | | |
| --- | --- | --- | --- | --- | --- | --- | --- | --- |
| Sample No. | Material | HTLV-III (Stock 21) $10^{-1}$ | Mixture CIM | AgSD | Stop Procedure | PEG Pellet Resuspended in (0.5 ml) | $Log_{10}$** $TCID_{50}$ Per/ml | Log*** Kill | Cytotoxicity |
| 1 | HTLV-III (Stock 21) $(10^{-1}$ | 60 ul | 540 ul | — | — | — | 4.5 | — | 0 |
| 2 | HTLV-III (Stock 21) $(10^{-1}$ | " | " | — | Column + Peg | CIM | 4.25 | — | 0 |
| 3 | 1% AgSD in 50% aqueous sucrose solution | " | — | 540 | Cent.* + Peg | CIM | 2.0 | 2.25 | 0 |
| 4 | 1% AgSD in 50% aqueous sucrose solution | — | — | 600 | Cent.* + Peg | $10^{-2}$ HTLV-III (Stop Control) | 3.25 | — | 0 |
| 5 | 0.5% AgSD in 25% aqueous solution | 60 ul | — | 540 | Cent.* + Peg | CIM | 2.25 | 2.0 | 0 |
| 6 | 0.5% AgSD in 25% aqueous solution | — | — | 600 | Cent.* + Peg | $10^{-2}$ HTLV-III (Stop Control) | 3.75 | — | 0 |

*Centrifuge 1 minute in microfuge - place supernatant on column
**$TCID_{50}$ = Tissue Culture Infecting Dose$_{50}$
***Compared to Sample No. 2

TABLE 2

| Drug During Incubation | (μg/ml) | Final (Drug) μg/ml | % Infection | % Infection v. Control |
| --- | --- | --- | --- | --- |
| chlorhexidine (CHA) | 10 | 2.5 | 3.35 | 108 |
| sodium deoxycholate (NaDC) | 40 | 10.0 | 3.35 | 108 |
| AgSD | 10 | 2.5 | 2.95 | 95 |
| AgSD + NaDC | 10 40 | 2.5+ 10.0 | 2.85 | 92 |
| AgSD + CHA | 5+ 5 | 1.25 + 1.25 | 2.45 | 72 |

TABLE 3A

| | Viable Cells/ml | | % Viab** |
| --- | --- | --- | --- |
| *AgSD | | | |
| 50 | 4 × 10⁵ | Cells in terrible condition. | 37 |
| 100 | 5 × 10⁴ | " | 0 |
| CHA | | | |
| 50 | 1.5 × 10⁶ | | 73 |
| 100 | 2.5 × 10⁵ | " | 20 |
| NaDC | | | |
| 50 | 1.2 × 10⁶ | | 73 |
| 100 | 2.0 × 10⁶ | | 44 |
| AgSD 50 + | 1.5 × 10⁴ | | 0 |

TABLE 3A-continued

| | Viable Cells/ml | % Viab** |
|---|---|---|
| CHA 50 | | |
| H₂O | $3.1 \times 10^6$ | 89 |
| Cells Alone | $3.0 \times 10^6$ | 88 |

*AgSD → insoluble. In an attempt to remove drug cells were spun at 200 g for 15 sec. (including acceleteration and deceleration time) → Cells pipetted off, then washed two times.

** $\frac{\text{live cells}}{\text{live \& dead}}$

TABLE 3B

Results
Rate of Killing of Macrophage by Drugs

| | % Kill |
|---|---|
| Control | 36 |
| AgSD (100 μg) | 100 |
| CHA (100 μg) | 100 |
| AgSD + CHA (50 μg + 50 μg) | 85 |

TABLE 4

Results

| Drug in Glove | Concentration of Drug in Coating Solution (%) | Weight of Spleen (mg) (Average of 6 Animals) | Weight Increase from Control (mg) |
|---|---|---|---|
| Silver sulfadiazine | 2 | 106 | 20 |
| Deoxycholate | 2 | 109 | 23 |
| Chlorhexidine | 2 | 234 | 148 |
| Silver sulfadiazine + deoxycholate | 1 + 1 | 115 | 29 |
| Silver sulfadiazine + chlorhexidine | 1 + 1 | 103 | 17 |
| Fusidic acid | 2 | 107 | 21 |
| Fusidic acid + Chlorhexidine | 1 +'1 | 319 | 23 |
| Control glove + PBS medium | | 86 | 0 |
| No glove - only PBS medium | | 86 | 0 |
| Control glove + RVB3 | | 1,627 | 1,541 |
| No glove + RVB3 | | 1,280 | 1,194 |

TABLE 5A

Rate of Killing of Candida-albicans by silver sulfadiazine an other agents on short exposure

| Drug | Concentration | Colony Counts in Culture (10 Minute Incubation) |
|---|---|---|
| Silver sulfadiazine | 100 | 10,000 |
| Chlorhexidine | 100 | 30 |
| Deoxycholate | 1,000 | 8,000 |
| AgSD + Chlorhexidine | 50 + 50 | 0 |
| AgSD + Deoxycholate | 100 + 100 | 20 |
| Nonoxynol | 0.2% | >50,000 |
| Control | | >50,000 |

3 ml of Saboraud broth containing $10^5$ organisms of Candida albicans were incubated with the above drugs. Aliquots were removed at 5 and 10 minutes and were subcultured.

TABLE 5B

Antibacterial Efficacy of Drug Coated Gloves against Candida albicans

Treated glove fingers were draped over the top of culture tubes with the treated side forming the inside of the cup shape. The 3.0 ml of TBS containing $10^3$ organisms of Candida albicans was dispensed in each finger and all placed in the water bath shaker at 37° C. Samples were removed at 15 minutes, 1 hour, 2 hours, and 4 hours. They were diluted 1-10 and plated on blood agar in 2.0 ml amounts.

| Drug in Glove | Colony Counts in Culture | | | |
|---|---|---|---|---|
| | 15 Minutes | 1 Hour | 2 Hours | 4 Hours |
| None (Control) | 1,400 | 2,000 | 4,000 | 6,000 |
| Chlorhexidine | 75 | 0 | 0 | 0 |
| Silver Sulfadiazine | 1,650 | 1,500 | 1,500 | 2,200 |
| Silver Sulfadiazine + Chlorhexidine | 0 | 0 | 0 | 0 |
| Silver Sulfadiazine + Deoxycholate | 1,500 | 400 | 0 | 0 |
| Silver Sulfadiazine + Chlorhexidine + Nonoxynol | 0 | 0 | 0 | 0 |

TABLE 6

Killing of Gonococcus by Silver Sulfadiazine and Other Agents

| Drugs | μg/ml | Colony Counts in Culture | |
|---|---|---|---|
| | | 5 Minutes | 10 Minutes |
| AgSD | 100 | 4,000 | 2,000 |
| Deoxycholate | 1,000 | 12,000 | 4,000 |
| Chlorhexidine | 100 | 2,000 | 10 |
| Nonoxynol | 0.1% | 40 | 70 |
| AgSD + Chlorhexidine | 50 + 50 | 0 | 0 |
| AgSD + Deoxycholate | 100 + 1,000 | 10 | 0 |
| None (Control) | | >50,000 | >50,000 |

Drugs were suspended in 5 ml of cultures containing $10^5$ organisms of gonococcus and incubated. Aliquots were removed at 5 and 10 minute intervals and subcultured for colony counts.

TABLE 7A

Toxicity of Drugs for HSV

One ml HSV at $3 \times 10^6$/ml was incubated with 200 μliters of drugs each 500 μg/ml stock solution. After 20 minutes at R.T., the virus was titered on monolayers of vero cells, incubated for 2 hours, then overlayed with methyl cellulose. Virus titers were read after 48 hours. No drug toxicity* was seen in rows titer read in.

| μliters added to 1 ml Virus | Titer | % Inhibition |
|---|---|---|
| 200 AgSD | $5.2 \times 10^5$ | 81 |
| 200 Chlorhexidine | $2.7 \times 10^6$ | 0 |
| 100 AgSD + 100 Chlorhexidine | $1.5 \times 10^4$ | 99.5 |
| 200 NaDC | $3.2 \times 10^6$ | 0 |
| 100 NaDC × 100 AgSD | $1.3 \times 10^6$ | 54 |
| 100 NaDC × 100 Chlorhexidine | $8 \times 10^4$ | 93 |
| 200 Benzalkonium choloride | $5.2 \times 10^4$ | 98 |
| 200 H₂O | $2.8 \times 10^6$ | 0 |
| 200 Media | $3.3 \times 10^6$ | 0 |

*Drug conc. in first row was 4–8μg/ml

TABLE 7B

Effect on HSV-1 of Interaction with Drug Treated Gloves

HSV-1 was diluted to $3 \times 10^6$ PFU/ml in DME 10% FCS. One ml of virus was placed in sterile drug treated gloves, incubated for 10 min. at room temperature then titered on Vero cells.

| Treatment | Titer (PFU/ml) |
|---|---|
| virus (no glove) | $2.9 \times 10^6$ |
| virus + control tube | $3.0 \times 10^6$ |
| virus + tube w | $4.3 \times 10^6$ |
| virus + tube x | <10 |

TABLE 7B-continued

Effect on HSV-1 of Interaction with Drug Treated Gloves

HSV-1 was diluted to $3 \times 10^6$ PFU/ml in DME 10% FCS. One ml of virus was placed in sterile drug treated gloves, incubated for 10 min. at room temperature then titered on Vero cells.

| Treatment | Titer (PFU/ml) |
|---|---|
| virus + tube y | <10 |

W = Silver sulfadiazine
X = Silver sulfadiazine + Deoxycholate
Y = Silver sulfadiazine + Chlorhexidine

We claim:

1. A method of inhibiting the transmission of AIDS virus in humans comprising topically applying an effective antiviral amount of an enhanced antiviral composition comprising an antiviral silver salt and an antiviral biquanide to a sexual canal of a human, wherein the silver salt and the biquanide are present in amounts such that the composition is effective to inhibit transmission of AIDS in humans.

2. A method according to claim 1, wherein the silver salt is selected from the group consisting of silver sulfadiazine, silver acetate, silver benzoate, silver carbonate, silver chloride, silver iodate, silver iodide, silver lactate, silver laurate, silver nitrate, silver oxide, silver palmitate, and silver salts of proteins.

3. A method according to claim 1, wherein the silver salt is silver sulfadiazine.

4. A method according to claim 2, wherein the biguanidine is chlorhexidine or a pharmaceutically acceptable salt thereof.

5. A method according to claim 2, wherein the antiviral composition further comprises an effective amount of a detergent.

6. A method according to claim 5, wherein the detergent is sodium deoxycholate.

7. A method according to claim 1, wherein the antiviral composition is a dispersion in a water-dispersible hydrophilic carrier.

8. A method according to claim 1, wherein the antiviral composition is a dispersion in a semi-soft or cream-like, water-dispersible or water-soluble oil-in-water emulsion carrier.

9. A method according to claim 1, wherein the antiviral composition is a dispersion in an aqueous sucrose solution.

10. A method according to any one of claims 1 to 3 and 4, 7, wherein the antiviral composition comprises from 0.1 to 10 percent by weight of the silver salt.

11. A method according to claim 1, wherein the antiviral composition is applied as a component of a lubricant material coating a penis.

12. A method according to claim 1, wherein the antiviral composition is applied as a component of a lubricant material applied to a condom.

13. A method according to claim 1, wherein the antiviral composition is applied as a coating to a device intended for insertion in a sexual canal.

14. A method according to claim 1, wherein the antiviral composition is applied as a component of an impregnant in a device intended for insertion in a sexual canal.

* * * * *

UNITED STATES PATENT AND TRADEMARK OFFICE
CERTIFICATE OF CORRECTION

PATENT NO. : 4,952,411

DATED : August 28, 1990

INVENTOR(S) : Fox, et al.

It is certified that error appears in the above-identified patent and that said Letters Patent is hereby corrected as shown below:

Title page, Item 73, after "Heights," insert --New York,--;
Title page, Item 56, 4th and 7th lines, "Wysur" should read --Wysor--;
Col. 1, line 35, "there" should read --their--;
Col. 3, line 52, "solution" should read --solution.--;
Col. 4, line 13, "combination-in-part" should read --continuation-in-part--;
Col. 6, line 9, "µl ml)" should read --(µl/ml)--;
Col. 6, line 9, "(5 µl ml)" should read --(5 µl/ml)--;
Col. 6, line 10, "(10 µml)" should read --(10 µl/ml)--;
Col. 9, line 9, "acceleteration" should read --acceleration--;
Col. 9, line 53, "an" should read --and--;
Col. 10, line 52, "100 NaDC x 100 AgSD" should read --100 NaDC + 100 AgSD--;
Col. 10, line 53, "100 NaDC x" should read --100 NaDC + --;
Col. 11, line 17, "biquanide" should read --biguanide--;
Col. 11, line 18, "biquanide" should read --biguanide--; and
Col. 12, line 17, "4, 7" should read --4 to 7--.

Signed and Sealed this

Twenty-first Day of April, 1992

Attest:

HARRY F. MANBECK, JR.

*Attesting Officer*  *Commissioner of Patents and Trademarks*